United States Patent [19]

McDonough

[11] Patent Number: 4,921,277
[45] Date of Patent: May 1, 1990

[54] METHOD OF LABELING NEEDLE SYRINGES AND MEDICATION VIALS AND NOVEL LABELS THEREFOR

[75] Inventor: Suellen McDonough, Durham, N.H.

[73] Assignee: Academy of Applied Science, Inc., Concord, N.H.

[21] Appl. No.: 261,841

[22] Filed: Oct. 24, 1988

[51] Int. Cl.⁵ .................. G09F 3/00; B42D 15/00; A61M 3/00; A61M 5/24

[52] U.S. Cl. ........................... 283/81; 40/316; 604/111; 604/187

[58] Field of Search ............ 283/79, 80, 81, 70; 604/110, 111, 187; 422/99; 156/DIG. 5; 40/316

[56] References Cited

U.S. PATENT DOCUMENTS

| | | |
|---|---|---|
| 257,136 | 4/1882 | Livor ............................ 283/81 |
| 3,228,129 | 1/1966 | Gwinn et al. ................. 283/81 |
| 3,648,838 | 3/1972 | Hiromura ...................... 283/81 |
| 4,208,588 | 6/1980 | Rudin .......................... 604/187 |
| 4,300,678 | 11/1981 | Gyure et al. ................. 604/111 |
| 4,312,523 | 1/1982 | Haines ......................... 283/81 |
| 4,656,767 | 4/1987 | Tarrant ......................... 40/316 |
| 4,708,368 | 11/1987 | Instance ....................... 283/81 |

Primary Examiner—Douglas D. Watts
Assistant Examiner—Paul M. Heyrana, Sr.
Attorney, Agent, or Firm—Rines & Rines

[57] ABSTRACT

Methods of labeling and novel labels for needle syringes and medication vials are provided, involving fool-proof transfer of medication information labels peelable from the vial and applied as a syringe label tag or flag remote from the syringe barrel calibrations and in no way impeding physical syringe operation.

5 Claims, 2 Drawing Sheets

METHOD OF LABELING NEEDLE SYRINGES AND MEDICATION VIALS AND NOVEL LABELS THEREFOR

The present invention relates to methods of labeling and improved label structures for needle syringes and the medication vials and the like from which the syringes withdraw the medication contents, so as to insure accurate identification of the contents in the syringe and to enable the ready display of further information such as dose, dilution, route of administration, patient's identification and location, or some of the above.

Serious accidents still occur in the operating room and elsewhere in the hospitals and in physician's offices, nursing homes and medical procedure clinics where medicine is withdrawn from vials by needle syringes without a fool-proof technique for avoiding unlabeled or mislabeled needle syringes and other identification mistakes of various types. Among present proposals for trying to minimize mistakes is the use of a simple adhesive tape which is handwritten upon by the person withdrawing the medicine and is hopefully attached to the syringe barrel. This procedure has several disadvantages including the partial obliteration of the syringe calibrations by the adhesive tape, the difficulty of recording upon that tape, the subsequent correct reading of what is written and the fact that lapses of memory can result in unmarked tapes or mis-marked tapes, particularly if other emergencies require postponement of the writing upon the tape or its application to the syringe. The stress of preparing for medical procedures and executing the same makes this a less than fool-proof identification technique. Another technique in common use involves going into a patient's unit with the vials and syringes and administering the same at the site. This, however, is very restrictive and can still result in errors particularly if the nurse is called away or interrupted in the procedure. This, furthermore, does not allow protection for specialized procedures where multiple medications are required to be available.

An object of the present invention, therefore, is to provide a new and improved method of fool-proof labeling and novel label structure for needle syringes and medication vials and similar devices from which the syringes are to withdraw medicines, that shall not be subject to the above-described disadvantages but that, to the contrary, provide a universally safe technique for contemporaneously and inherently totally accurately identifying the medication withdrawn by the needle syringe while at the same time providing labeling space, if desired, for patient identification, route, dose, amounts, times and other data necessary for safe identification, association and use of the syringe; and effecting such in a manner that, while the label is attached to the syringe in a positive way, does not cover or interfere with the visual observation of syringe calibrations or contents.

Other and further objects will be explained hereinafter and will be more particularly delineated in the appended claims.

In summary, however, from one of its aspects, the invention involves a method of labeling syringes and vials from which the syringes withdraw medication, that comprises, applying a pressure-sensitive adhesively backed removable medicine-identifying label to a vial containing the medicine; inserting a needle syringe into the vial to withdraw the medicine; peeling the medicine-identifying label from the vial; and applying the label as a tag extending to the side of the syringe and secured thereto along a narrow strip of the syringe barrel near its upper opening remote from the barrel calibrations. In one form, the label tag and an integral adhesively backed narrow strip is directly applied near the opening or plunger end of the syringe after peeling the same from the vial; and in a second embodiment, such a label-strip is separately provided and a vial medicine-identifying label is peeled from the vial and applied to the label-strip structure.

Preferred and best mode embodiments and details are hereinafter presented.

The invention will now be described in connection with the accompanying drawings, FIG. 1 of which is an isometric view of a medicine-containing vial bearing a novel identification label and a syringe for withdrawing medicine through the needle-pierced rubber cover section of the top of the vial;

Figure 1:
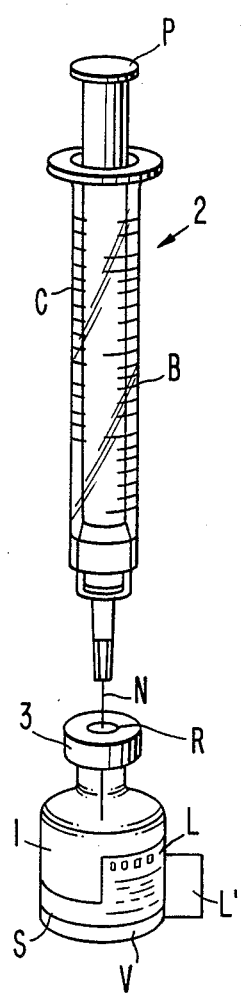
Figure 2:
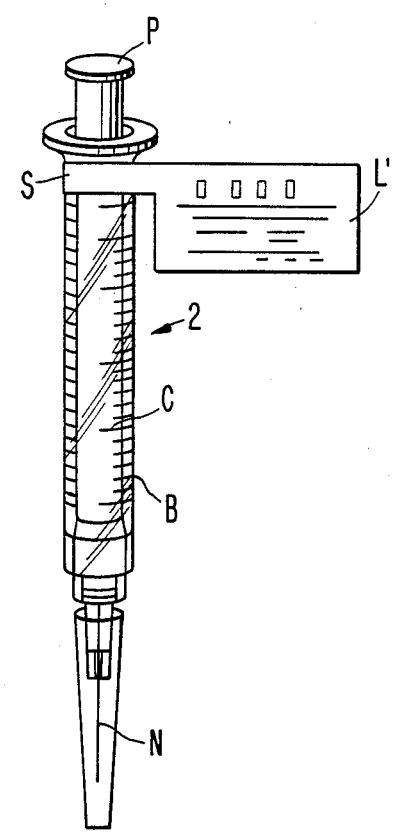
FIG. 2 is a view similar to FIG. 1 with the label stripped from the vial and applied to the syringe barrel adjacent to its upper flanged open end at which the plunge is received.

Referring to FIG. 1 of the drawing, a conventional medicine-containing vial is shown at V bearing its content-identifying label L and a supplemental duplicative identifying label L' which is secured as a tab or flag by a tinner integral narrow wrapable or flexible strip extension S removably adhered to the vial as by pressure-sensitive adhesive. A syringe 2 with its plunger P inserted within the flanged top opening of the outer cylinder barrel B containing measurement calibrations C printed upon the outer surface is shown with its needle N inserted through the penetrable self-sealing rubber top cover or insert R in the vial cap 3 to enable the withdrawal of the vial medication upwardly into the inner chamber of the barrel B in well-known fashion. In accordance with the present invention, as more particularly shown in FIG. 2, before the syringe is separated from the vial, the strip S together with its label flag or tag L' preferably stiffer and self-supporting, is thereupon stripped from the vial V and immediately applied to the upper neck of the barrekl B just below the top opening flange. In view of the thinness of the strip S, it neither obscures or otherwise interferes with the reading of the calibrations or the inspection of the medicine in the syringe, and the flag or tag L', held to the side, inherently and in fool-proof fashion, positively and reliably identifies the medicine in the syringe.

If desired, the label L'-S may serve as the only label of the vial, removable as above described, but this would appear to be less desirable since it would result in a labelless vial when removed.

While this procedure is quite convenient, it is not necessary, however, that a vial label itself actually be removed from the vial as in the embodiments of FIGS.

Figure 3:
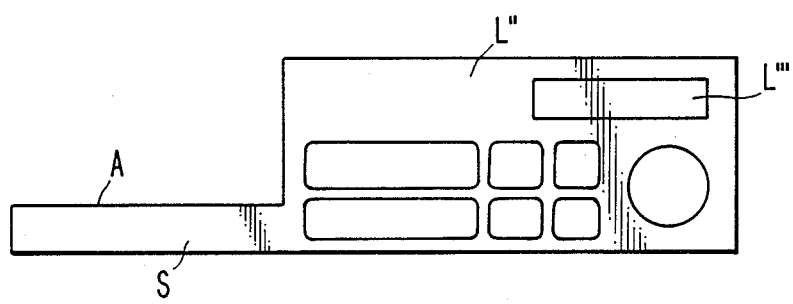
FIG. 3 is a plan view of a preferred label.
Figure 4:
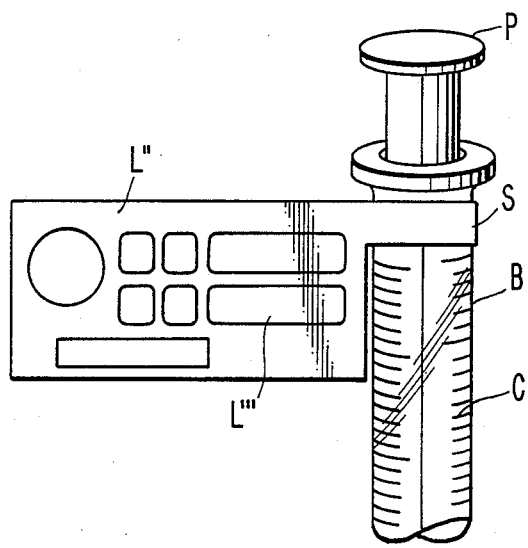
FIG. 4 is an isometric view upon a somewhat larger scale that FIG. 2 of the syringe with the label of FIG. 3 attached to its barrel adjacent to its plunger-receiving open end.
Figure 5:
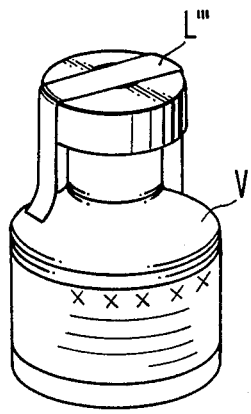
FIG. 5 is an isometric view of a vial, upon a larger scale than FIG. 1, with a pressure-adhesive supplemental label identifying the vial medication and attached to the top cap of the vial for removal and application to the syringe label.

1 and 2. The identification tags and labels may be made in a similar form to the label L'-S of FIGS. 1 and 2 but be separately supplied as at L"-S in FIG. 3 and applied in a manner similar to the label L'-S of FIG. 2, as more particularly shown in FIG. 4. This separate label structure L" (somewhat larger than L' in FIG. 2) is also integrally provided with a narrow wrapable or flexible strip extension S, pressure-sensitive adhesively backed at A, and with the label or tag or flag portion L" provided with enough space for the entry of patient name, dose, quantity, route, time, and other information and, most importantly, a medicine-identifying pressure-sensitive adhered label L" peeled from the vial, such as at the top in FIG. 5. While, if necessary, the name of the medication may be written by the practitioner in an appropriate space on the label L", which should be stiff enough for such purpose, the fool-proof feature of the invention requires the pressure-adhesive-attached strip L" containing the vial medication identification to be peeled off from the vial cap or from some other surface portion of the vial and immediately adhered to the main label L", as shown in FIG. 4.

Figure 6:
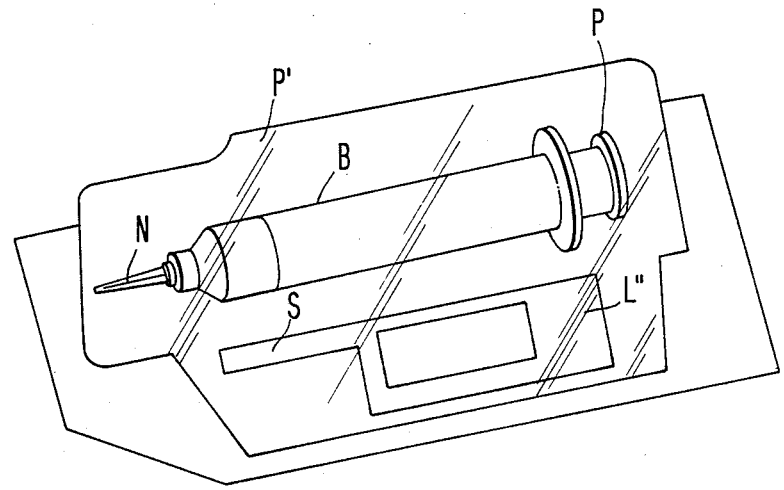
FIG. 6 is a similar view of a sterilized package containing syringe and the label of FIG. 3.

Through this technique, when a sterile syringe package P', FIG. 6, is opened, for example in the operating room, and the syringe is permitted to enter the sterile field, the label S-L" also sterilized as by gas sterilization, will also be available for immediate attachment to the syringe barrel for marking with a sterile pan. If desired, a removable release paper strip, not shown, may be applied to the adhesive side of the strip S.

Through these concepts, therefore, reliable permanent tagging identification of the syringe contents is achieved and with a self-supporting identifying tag or flag to the side of the syringe not interfering with the physical operation of the syringe and not masking any of the visibility requirements thereof.

Further modifications will also occur to those skilled in this art and such are considered to fall within the spirit and scope of the invention as defined in the appended claims.

What is claimed is:

1. A method of labeling syringes and vials from which the syringes withdraw medication, that comprises, applying a pressure-sensitive adhesively backed removable medicine-identifying label to a vial containing the medicine; inserting a needle syringe into the vial to withdraw the medicine; peeling the medicine-identifying label from the vial; and applying the label as a tag extending to the side of the syringe and secured thereto along a narrow strip of the syringe barrel near its upper opening remote from the barrel calibrations.

2. A method as claimed in claim 1 in which the steps are performed of providing the medicine-identifying label with an integral narrow strip, coating the same with the pressure-sensitive adhesive, and applying the same as the label to the vial and, following removal from the vial, wrapping, the said narrow strip around the syringe barrel remote from the calibrations to secure the label as a self-supporting tag extending to the side of the syringe.

3. A method as claimed in claim 1 and in which the steps are performed of providing the syringe with a label having a narrow integral strip, coating the same with the pressure-sensitive adhesive and wrapping the same around said narrow strip of the syringe barrel to secure the label extending as a self-supporting tag to the side of the syringe, and peeling the medicine-identifying label from the vial and adhesively applying it to said side-extending label as a part thereof.

4. A method as claimed in claim 2 in which the step is performed of sterilizing said label with its integral narrow strip with the syringe in a sterile package for use in the operating room.

5. A label for identifying needle syringes which withdraw medication from a vial or the like, having, in combination, an identification label tag of sufficient width to record information as to one or more of patient identification, dose, route, time and other data, the said label being provided with an integral pressure-sensitive adhesive-backed strip extending from the label and substantially narrower than the same and of flexibility and length sufficient to wrap around the plunger end of the syringe barrel along a narrow strip thereof remote from the barrel calibrations, with the label thus extending to the side of the barrel as a self-supporting tag or flag.

* * * * *